United States Patent [19]
Levin et al.

[11] Patent Number: 4,576,602
[45] Date of Patent: Mar. 18, 1986

[54] BLOW MOLDED CONTAINER WITH INTEGRAL ADMINISTRATION PORT

[75] Inventors: Harold A. Levin, Grayslake; Mark E. Larkin, Lindenhurst, both of Ill.

[73] Assignee: Abbott Laboratories, North Chicago, Ill.

[21] Appl. No.: 578,161

[22] Filed: Feb. 8, 1984

[51] Int. Cl.[4] ............................................. A61B 19/00
[52] U.S. Cl. .................................... 604/408; 604/415
[58] Field of Search ....................... 604/408, 403, 415

[56] References Cited

U.S. PATENT DOCUMENTS

| | | | |
|---|---|---|---|
| 3,215,299 | 11/1965 | Coanda et al. | 604/403 X |
| 3,746,001 | 7/1973 | Ralston, Jr. | 128/214 D |
| 3,955,833 | 5/1976 | Silbert | 285/3 |
| 4,049,033 | 9/1977 | Ralston | 604/408 |
| 4,088,166 | 5/1978 | Miller | 604/408 |
| 4,096,897 | 6/1978 | Cammarata | 604/408 |
| 4,240,481 | 12/1980 | Bayham | 150/8 |
| 4,279,352 | 7/1981 | Ward | 215/247 |
| 4,303,067 | 12/1981 | Connolly et al. | 604/408 |
| 4,393,909 | 7/1983 | Pearson | 150/8 |
| 4,441,538 | 4/1984 | Larkin et al. | 604/415 |
| 4,484,916 | 11/1984 | McPhee | 604/415 X |

Primary Examiner—G. L. Kaplan
Attorney, Agent, or Firm—Neil E. Hamilton; Alan R. Thiele; Michael J. Roth

[57] ABSTRACT

A port system for a blow molded intravenous solution container in which microbial contamination is prevented upon administration of the solution. The port system includes an integrally formed tube projecting outwardly from the container with a pierceable diaphragm positioned over the entry portion of the tube. Preferably, with respect to the tube entry portion, the diaphragm is concave, and may be made thinner in the center to facilitate proper placement of a piercing pin. In one embodiment, the port tube is inwardly flared adjacent the diaphragm so that as the piercing element is pushed through the diaphragm, the remnants of the pierced diaphragm can be pressed into the flared portion of the tube.

10 Claims, 24 Drawing Figures

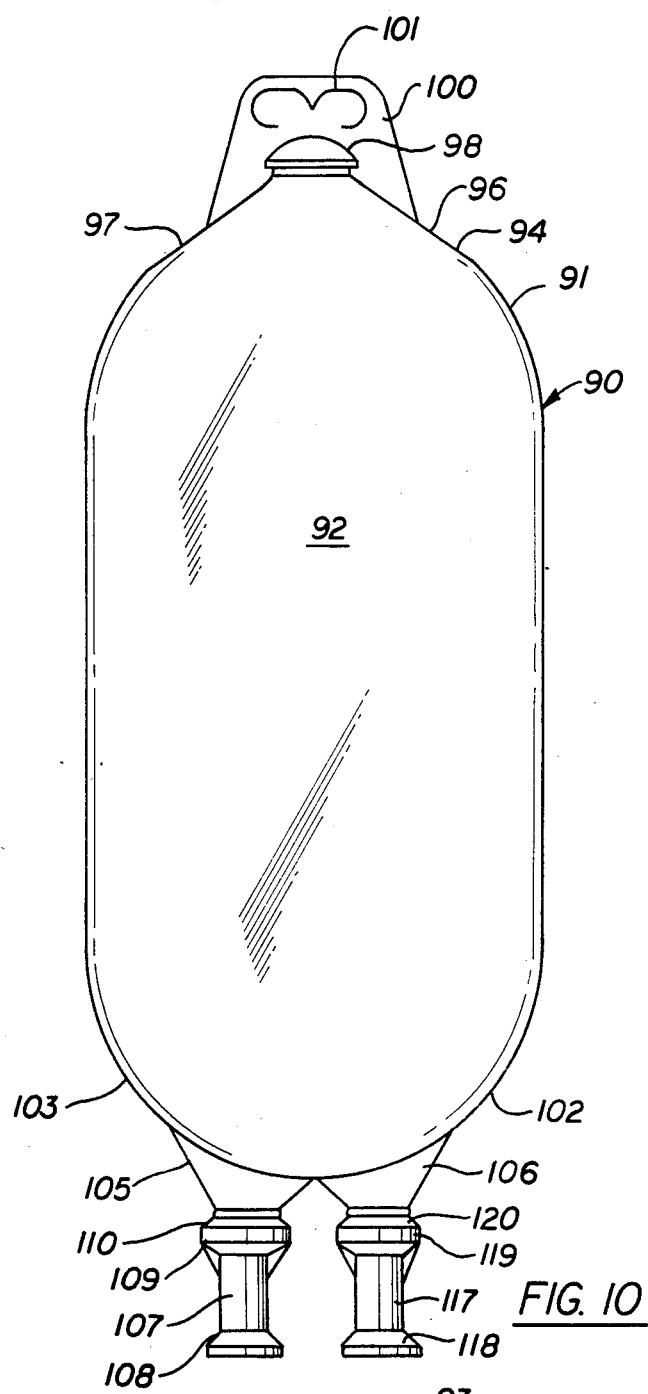
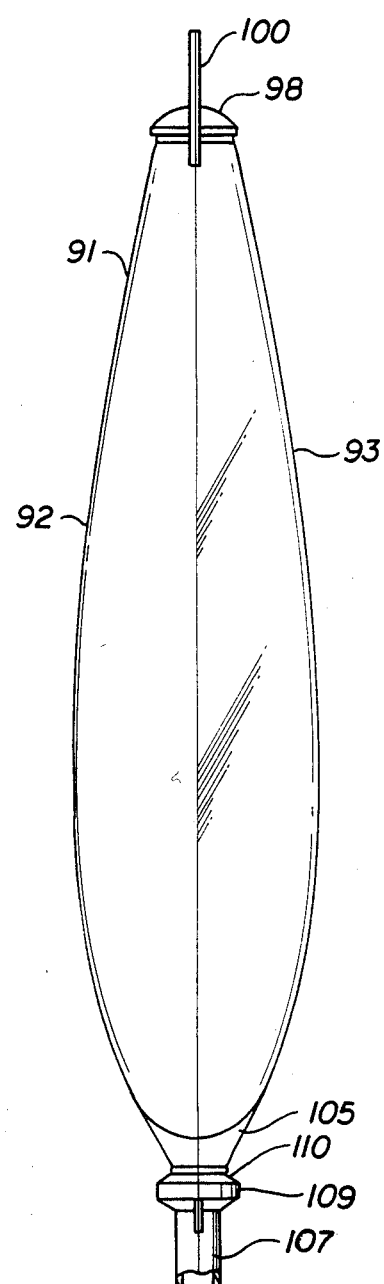
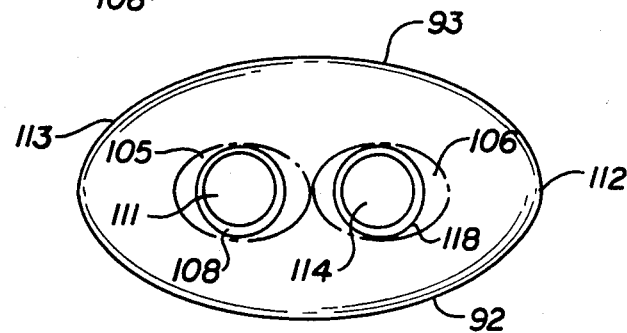
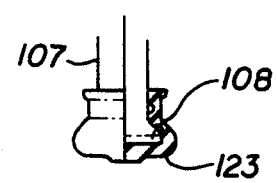
FIG. 10
FIG. 11
FIG. 12
FIG. 13

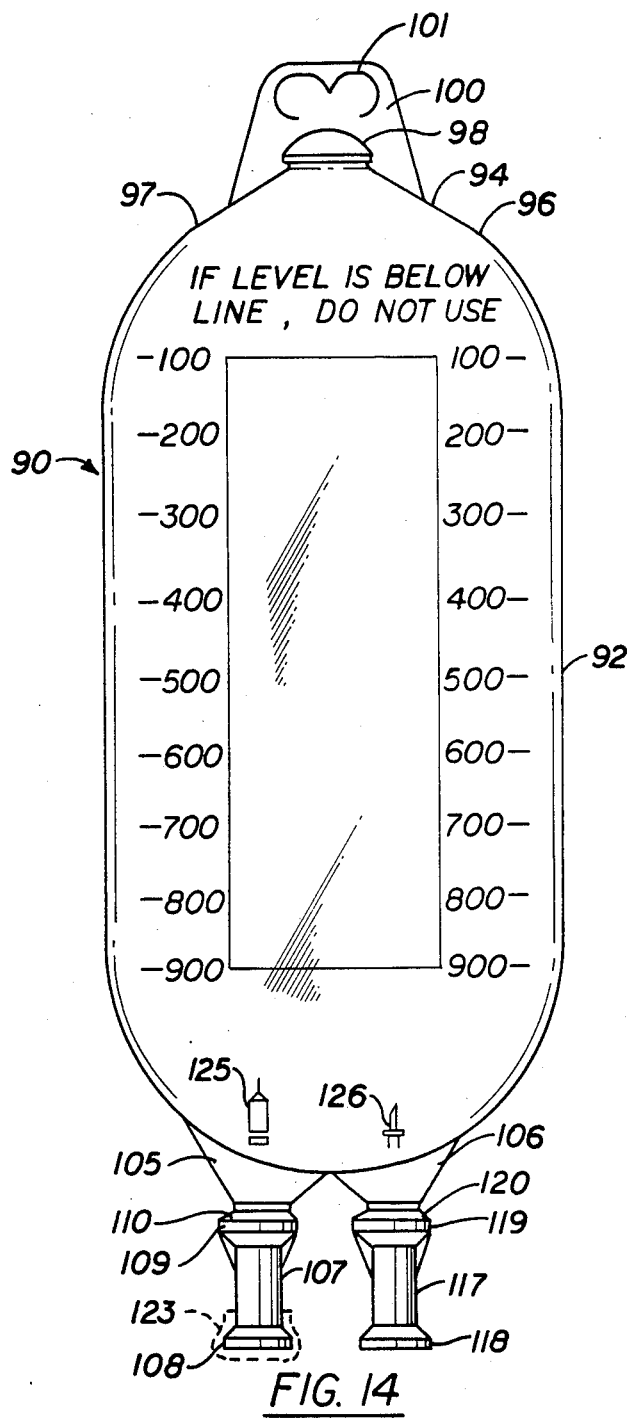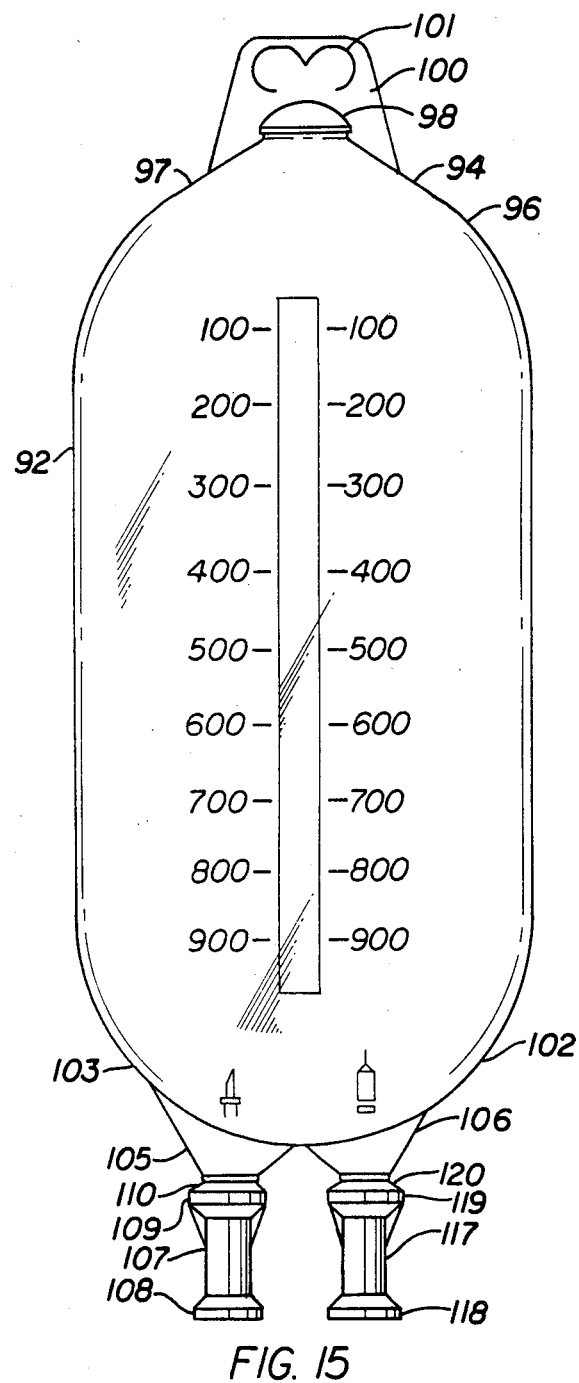
FIG. 14
FIG. 15
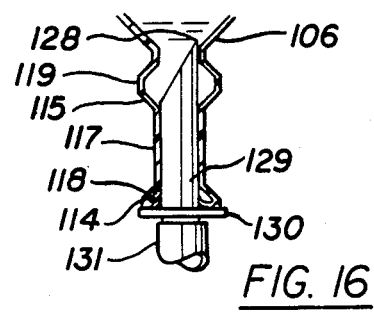
FIG. 16

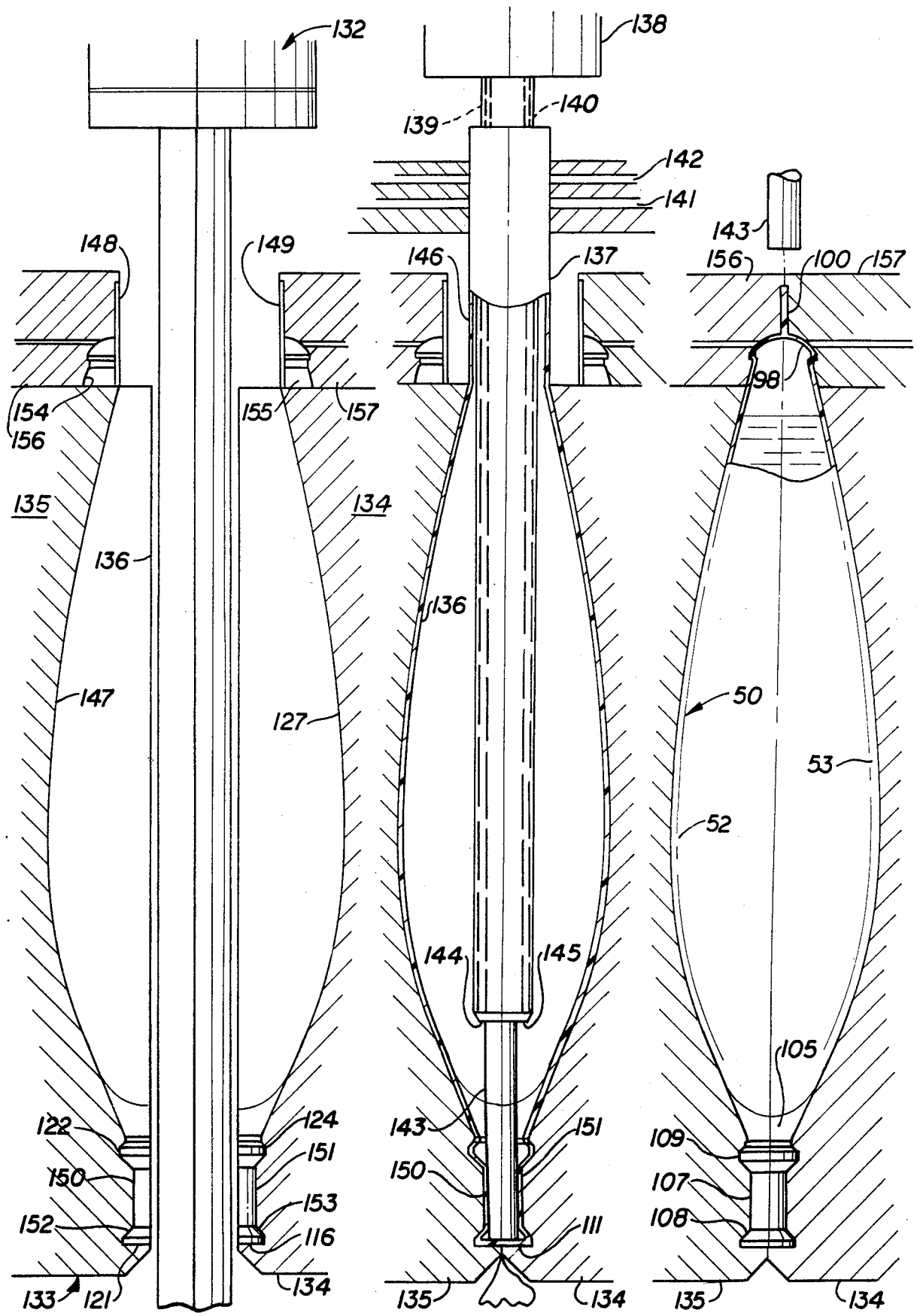

BLOW MOLDED CONTAINER WITH INTEGRAL ADMINISTRATION PORT

BACKGROUND OF THE INVENTION

This invention relates to a port system for a blow molded container wherein the port system is designed to reduce microbial contamination during usage. More particularly, this invention relates to a blow molded container wherein the port system is simultaneously formed with the container and includes a pierceable diaphragm which is disposed over the mouth of the tube with the diaphragm constructed in an inwardly positioned concave manner and the tube being flared inwardly so as to provide efficient piercing by the piercing pin as well as placement of the remnants of the pierced diaphragm.

An administration port with a diaphragm especially designed to receive a piercing pin in a sealing manner is described in U.S. Pat. No. 4,393,909. In U.S. Pat. No. 3,746,001, a blow molded container is described having a port with a diaphragm in a specially designed flexible tube formed as one of the ports. In U.S. Pat. No. 4,279,352 a unitary molded injection site is described and a double diaphragm arrangement for a container and piercing pin is described in U.S. Pat. No. 3,955,833. In U.S. Pat. No. 4,240,481 an openable seal member for a flexible container is described having flexible and generally conical portions.

Nowhere in the prior art is there described a unitary port and diaphragm as well as a container wherein the port stucture and the diaphragm are specially designed to receive the piercing pin in an easy open manner. Neither does the prior art illustrate a blow molded container with a unitary fluid-type seal which effects administration of the container contents without substantial risk of contamination.

It is an advantage of the present invention to provide an integral administration port for a blow molded container which minimizes molding steps and the use of additional components. Other advantages are a port structure for a flexible container wherein a piercing spike can be easily received and yet provide a fluid-type seal; a port structure for a blow molded I.V. solution container which offers the option of placement of protective components if desired; a port structure for an I.V. solution container which will receive a piercing spike having an additive port and a port structure for a blow molded container which accomplishes all of the foregoing features, yet can be blow molded into various geometric configurations so as to meet various molding parameters.

SUMMARY OF THE INVENTION

The foregoing advantages are accomplished and the shortcomings of the prior art are overcome by the flexible collapsible container of this invention which includes a body section of a generally tubular configuration when empty having a longitudinal axis and a transverse axis shorter than the longitudinal axis. The body section, when filled with medical or I.V. fluid, will have a generally transverse oval configuration. The body section presents front, back, side and opposing end walls which are substantially smooth and unencumbered. The side walls at one end of the body section taper from the outermost dimension of the body section to the hanger section to provide shoulder portions. One of the end wall portions provides a hanger section and the other a tubular passageway with a diaphragm. The body section of the container and a tubular passageway with the diaphragm are formed in a one-piece construction with the diaphragm positioned adjacent the outward end of the tubular passageway. The tubular passageway and the diaphragm are constructed to receive a piercing pin in a manner such that portions of the pierced diaphragm can be received in the tubular passageway and yet provide a fluid-tight seal with the piercing pin or spike. In a preferred manner, the tubular passageway includes a frusto-conical portion at the outer end with the diaphragm position therein. In one embodiment, the diaphragm is positioned inwardly of the tubular passageway and is formed in a concave manner with the smallest portion placed inwardly in the tubular passageway. In one embodiment, the port structure will include a larger diameter intermediate section positioned between the tubular passageway and the body section of the container. If desired, the intermediate section can include a circumferential groove or a ledge to receive a cap or cover member. In another embodiment, the diaphragm is positioned outwardly of the frusto-conical portion extending from a straight wall portion. Preferably, the tubular passageway is formed with a stepped parting line so that the formed diaphragm can be more easily punctured with a piercing spike. If desired, a rubber reseal device can be secured over the frusto-conical portion. Alternatively, if one port member is utilized, it is adapted to receive a piercing spike having an additive port thereon.

BRIEF DESCRIPTION OF THE DRAWINGS

A better understanding of the port structure and container of this invention will be had by the following description taken together with the accompanying drawings, wherein:

FIGS. 10, 11, 12 and 13 are similar to FIGS. 1-4, respectively, showing still another alternative embodiment.

FIGS. 14 and 15 are views in side elevation showing still another embodiment of this invention.

FIG. 16 is a detailed view in vertical section illustrating the piercing of one of the port structures of the container shown in FIGS. 14 and 15.

FIGS. 22, 23 and 24 are views primarily in vertical section showing the molding operation of the containers of this invention.

DESCRIPTION OF THE EMBODIMENTS

Figure 1:
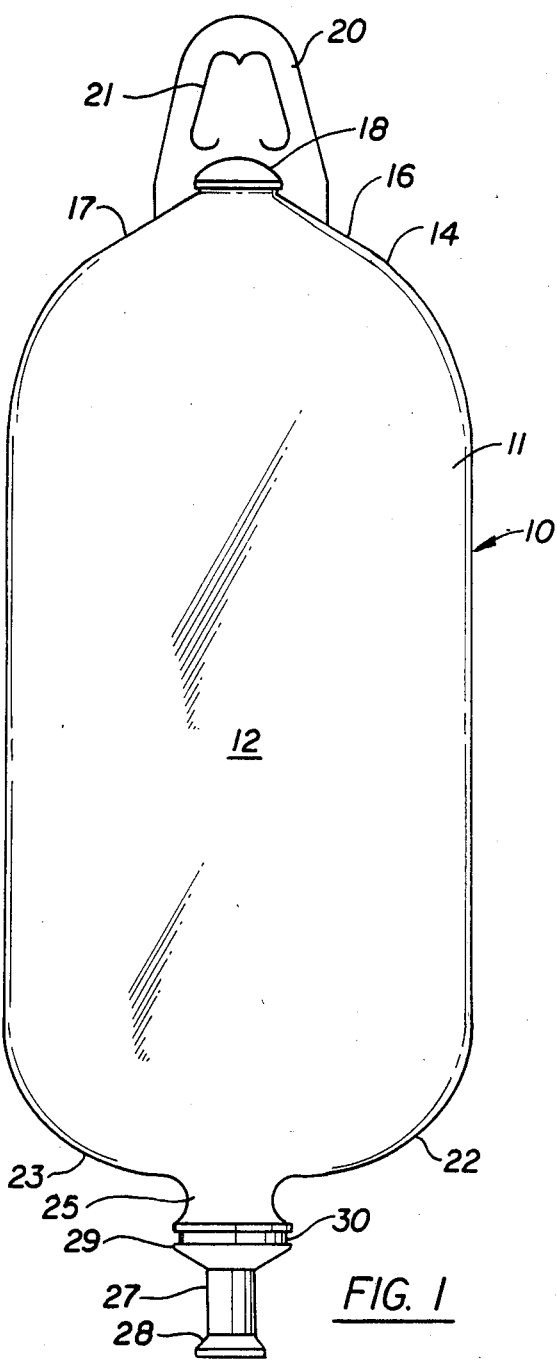
FIG. 1 is a view in side elevation of one embodiment of this invention illustrating the container and the integrally formed port structure.
Figure 2:
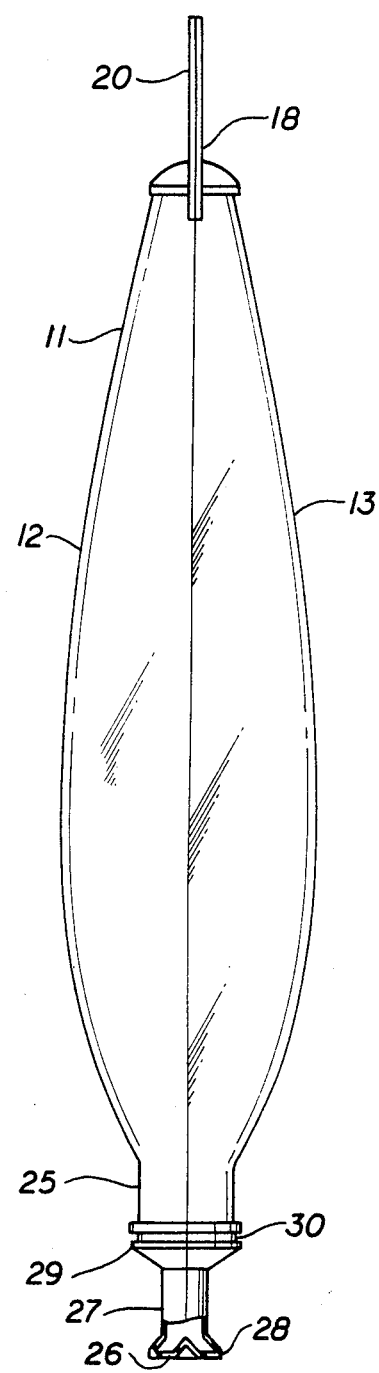
FIG. 2 is a view in side elevation of the container and port shown in FIG. 1.
Figure 3:
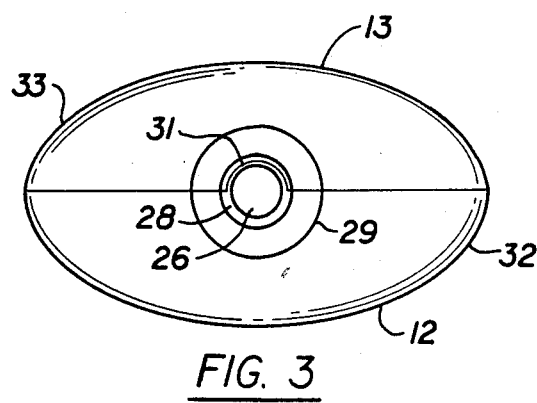
FIG. 3 is a bottom view of the container and port shown in FIG. 1.

Referring to FIGS. 1-4, flexible container generally 10 includes a tubular body section 11 with front and back walls 12 and 13 respectively, as well as an end wall 14 with shoulder portions 16 and 17. Extending from end wall 14 is a dome section 18 surrounded by a hanger section 20 with a tear detail 21. At the opposite end there are base portions 22 and 23 from which extends tubular port 25. Tubular port 25 includes an outer frusto-conical portion 28 with a diaphragm 26 disposed therein. Extending from portion 28 is a tubular passageway 27 communicating with an intermediate section 29. A groove 30 is formed circumferentially in intermediate section 29 to receive a flange 35 of a protective cover 36. As indicated in FIGS. 1 and 2, diaphragm 26 is formed in a slight inward concave manner so as to form a "target" area for the piercing pin. In FIG. 3, it will be seen that there is a parting line 31 in frusto-conical section 28. This is effected during the molding operation as will be explained later so as to avoid having a parting line in diaphragm 26.

FIGS. 5-8 illustrate a further embodiment generally 50 of the container and port system with numeral 51 designating the tubular body section and numerals 52, 53 and 54 designating front, back and end walls respectively. Rounded shoulder sections 56 and 57 are indicated in this embodiment with dome section 58 surrounded by a hanger tab 60 which has a more flattened profile than hanger tab 20 and also includes a tear detail 61. Body section 51 also includes side walls 72 and 73 and base portions 62 and 63 extend from the opposing end with a tubular port 65 extending therefrom. It will be noted that tubular port 65 differs from tubular port 25 in having a more slender profile. Port 65 has an enlarged intermediate section 69 as well as a tubular passageway 67 terminating in frusto-conical portion 68 with a diaphagm 78. In this embodiment, cover 76 with flange 75 will engage ledge 70 on intermediate section 69 for securing purposes.

Figure 9:
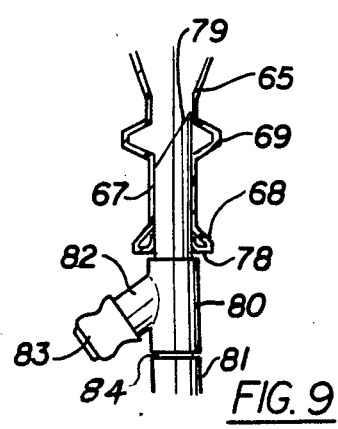
FIG. 9 is a detailed view in vertical section of the port structure shown in FIGS. 5-8 receiving a piercing spike with an additive port.

Referring to FIG. 9, piercing spike 79 is shown in operative engagement with and inside passageway 67, as will be seen from the fact that diaphragm 78 has been pierced. A hub portion 80 has extending therefrom a side arm 82 additive port with a reseal plug 83. Flexible tubing 81 will extend in fluid tight communication from hub 80 adjacent thereto by connection with reduced diameter section 84.

Figure 8:
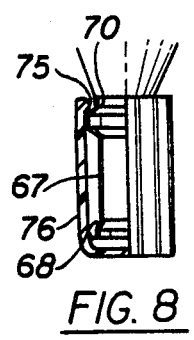

FIGS. 10-15 show another flexible container system generally 90, and similar to the previous embodiments, has a tubular body section 91 with front, back and end walls 92, 93 and 94 respectively. Rounded shoulder portions 96 and 97 are formed at one end of the container as well as the dome section 98 surrounded by a hanger tab 100 with a tear detail 101. Tubular body section 91 includes side walls 112 and 113, two tubular ports 105 and 106 will extend from base portions 102 and 103. Ports 105 and 106 will have tubular passageways 107 and 117 as well as frusto-conical portions 108 and 118 with diaphragms 111 and 114, respectively. Intermediate sections 109 and 119 are also provided, as well as ledges 110 and 120 for the purpose of receiving a cover such as 76 (FIG. 8). As will be seen in this embodiment 90, tubular passageway 107 will receive a rubber reseal 123 over the frusto-conical portion 108. As seen in FIGS. 14 and 15, front wall 92 can be provided with the usual numerical indicia showing volume as well as contents of the container. Additionally, diagramatic indicia can be indicated such as at 125 and 126 in the form of symbols to indicate the proper usage of the respective ports.

FIG. 16 illustrates the piercing of diaphragm 114 by piercing spike 129. Flange 130 will act as a stop for piercing point 128 which will preferably extend only a short distance beyond intermediate section 119.

Figure 17:
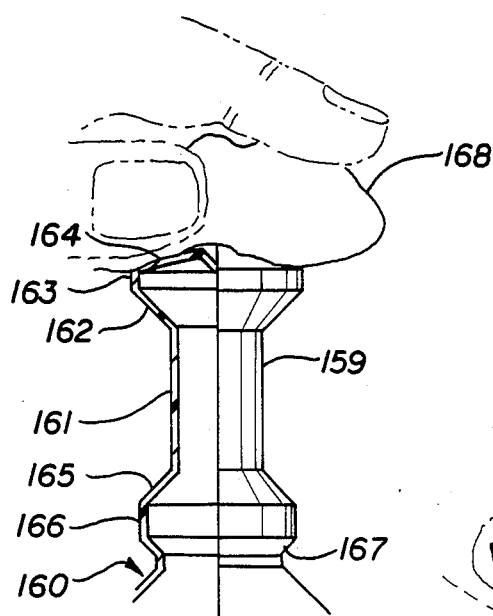
FIGS. 17-21 are enlarged views in partial vertical section of another embodiment of the port structure of this invention illustrating a piercing sequence with a piercing pin.

Referring to FIGS. 17-21, flexible container generally 160 will include tubular port 159 having a tubular portion or passageway 161 which is innerconnected to container 160 by means of a diverging wall portion 165, and straight-wall portion 166 and a converging portion 167. At the opposite end of tubular portion 161 is a diverging portion 162, a straight-wall portion 163 and the converging and covering diaphragm 164 which in this case is substantially convex in configuration. In FIG. 17, a sponge 168 with aseptic material would be utilized to wipe over diaphragm 164 prior to contact with spike 129 having piercing point 128 and flange 130. The advantages of flexible container 160 as well as tubular port 159 will be described later in the Operation.

A method of forming and filling the containers of this invention and particularly container 50 is illustrated in FIGS. 22, 23 and 24. The customary forming, filling and sealing techniques will be employed as seen in these Figures. An extruder head generally 132 is utilized in conjunction with mold, generally 133, having mold halves 134 and 135 with cavities 147 and 127 having a contour of the desired end shape of the container. Mold 133 will also include head portions 156 and 157 with dome cavities 154 and 155 respectively as well as respective pinch portions 148 and 149. A parison 136 will be dropped through the mold halves in the usual manner in between pinch portions 148 and 149 as well as port cavity portions 150, 151 with enlarged sections 122, 124 and frusto-conical cavities 152, 153. After parison 136 is dropped it will be transferred to blow fill head 138 as shown in FIG. 23. Air will be supplied and will expand parison 136 by means of air channel 139 and air orifice 144. Liquid will be later supplied to the actually formed container when mold halves 134 and 135 contract in the area of tubular cavities 150, 151, and liquid will be supplied through liquid channel 140 and liquid orifice 145. During this contraction, a diaphram 111 will be formed with previously described concave configuration. This is accomplished by contouring mold portions 134 and 135 in the area indicated by numerals 121 and 116 in conjunction with forming pin 143 having a convex end portion. As illustrated in FIG. 24, forming pin 143 will be retracted after forming the diaphragm 111 and mold head sections 156 and 157 will contact and provide the hanger tab 100 over dome section 98 between pinch portions 148 and 149. It will be appreciated that during the customary filling procedure illustrated in FIG. 23 a vacuum will hold the parison 136 open and will be supplied through vacuum lines 141, 142. In a preferred manner, diaphragm 111 will be formed with a thinner wall portion in the center than at the edges. This facilitates the piercing by a piercing pin such as 129. Also by means of molding with a stepped parting line (as seen in FIG. 3) the diaphragm will be fabricated with an offset parting line, which also facilitates ease of piercing.

OPERATION

Figure 18:
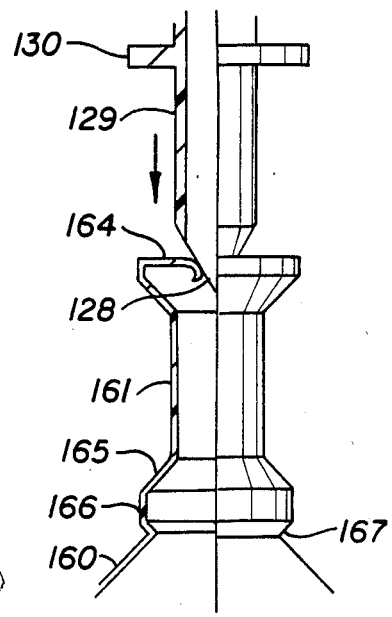
Figure 19:
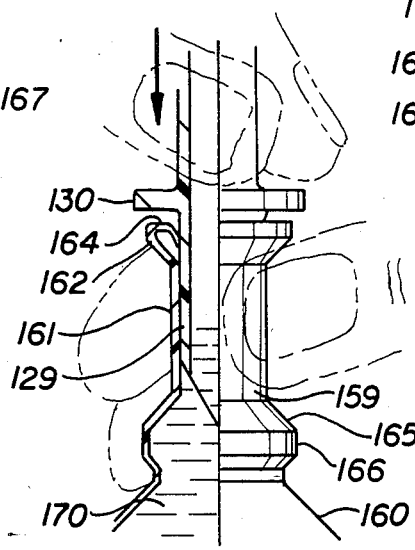
Figure 20:
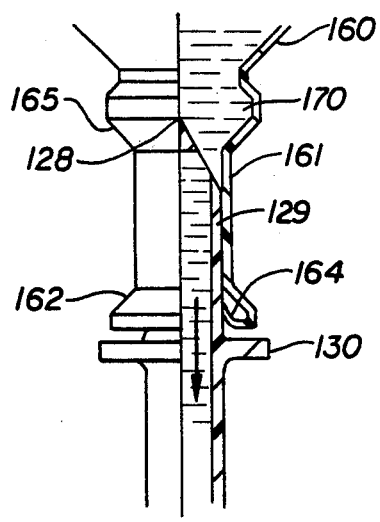
Figure 21:
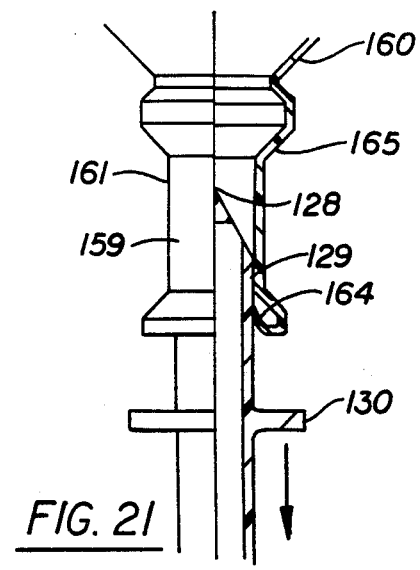

While the usage of the container port system herein described should be obvious from the previous description, a brief indication of its usage will be made. As indicated earlier, an important aspect of this invention is in the simplified formation of the diaphragms 26, 78, 111, 114 and 164 in conjunction with the respective port structures. This advantage is further seen by the manner in which a piercing spike such as 129 pierces through the respective diaphragms with the remnants of the diaphragms being accommodated within the frusto-conical wall portions. For example, in FIG. 16, it will be seen that the broken or remnants of diaphragm 114 are accommodated against the piercing pin 129 and hence the frusto-conical wall portion 118. This offers a tight seal with the pin as well as its contact inside the passageway 115 of tubular port portion 117. In embodiment 160, although the diaphragm 164 extends outwardly, it will be seen in conjunction with FIGS. 19, 20 and 21 that when piercing spike 129 pierces through diaphragm 164 it will move the diaphragm inwardly as seen in FIG. 18 with the remnants being accommodated inside diverging wall portion 162 as in FIG. 20. FIG. 19 depicts the manner in which the spike 129 and tubular port 159 will be gripped during piercing and seating of the pin. FIG. 21 illustrates that piercing pin 129 can be easily withdrawn from port 159 as diaphragm 164 will slide easily over piercing pin or spike 129.

Figure 4:
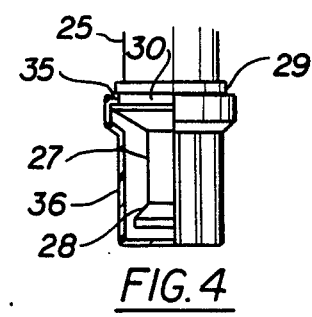
FIG. 4 is a detailed view of the port structure of FIG. 1 illustrating a cover in partial vertical section.
Figure 5:
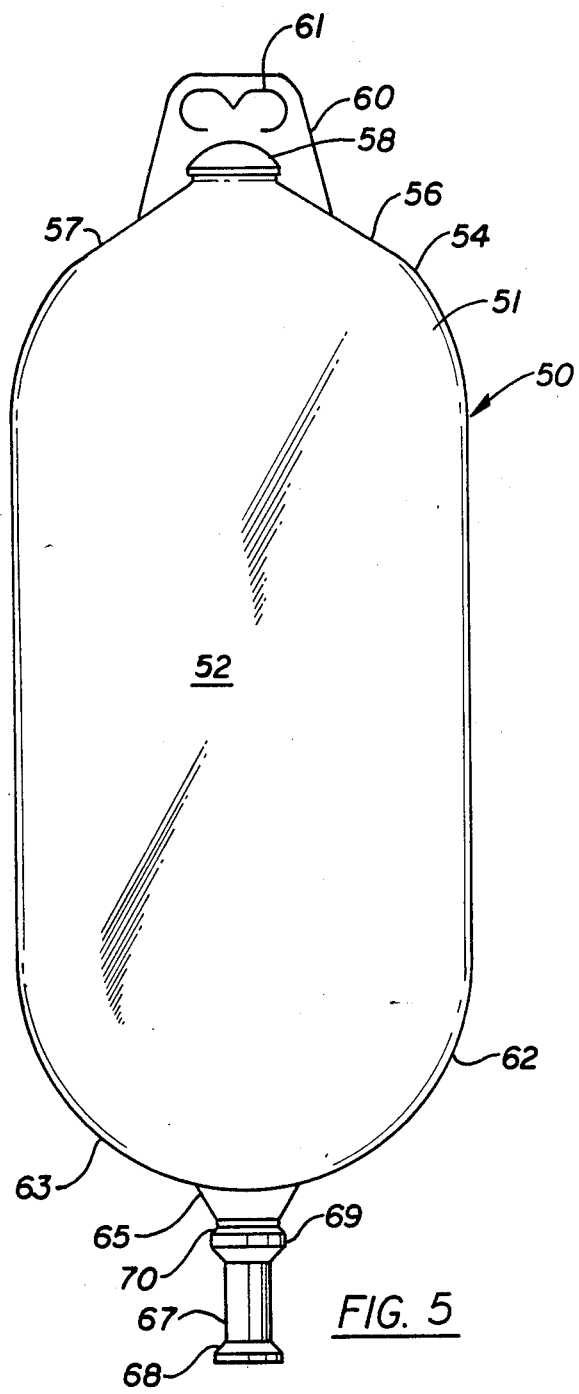
FIGS. 5, 6, 7 and 8 are views similar to FIGS. 1, 2, 3 and 4, respectively, showing an alternative embodiment.
Figure 6:
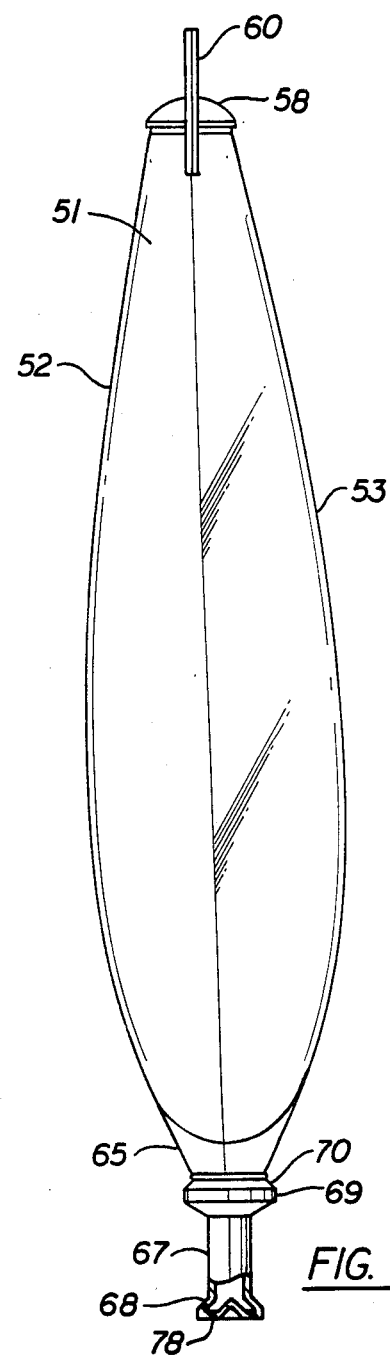
Figure 7:
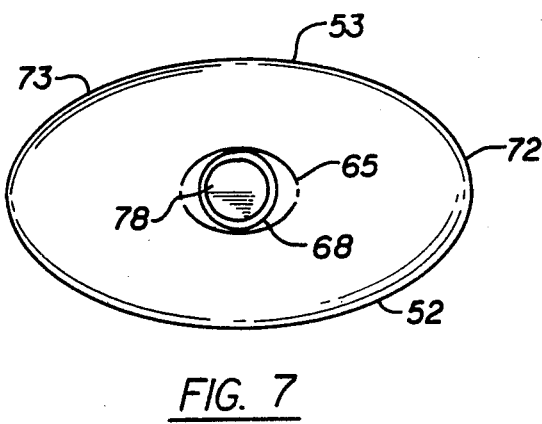

The versatility of the container port system of this invention is seen in the fact that if desired, a closure or cover 36 can be applied to the port as seen in FIG. 4. If desired, a rubber reseal 123 unit which is illustrated in FIG. 13 can also be placed over the frusto-conical portion 108 of the port 105. Alternatively, if only one port system is utilized such as indicated with containers 10 and 50, a spike 79 can be utilized with an additive port 83.

The preferred resin for blow molding the containers with the integral ports and diaphragms of this invention is polyvinylchloride. However, other resins such as polypropylene or polyethylene could be employed. The various piercing spikes are fabricated of the usual plastic materials such as A.B.S., acetals, or polypropylene. They will be secured to flexible tubing, such as 131, in a typical I.V. administration set to deliver I.V. liquid 170 from the container such as 160.

It will thus be seen that through the present invention there is now provided a container and port system which is simplified in its construction, yet is easily molded, employing a minimum number of components; a container and port system which readily accommodates a piercing pin with a fluid tight connection. The versatility of the present container system is seen in the fact that, if desired, various components such as rubber reseal units are readily applied as well as protective cover members. No new molding techniques need be employed to fabricate the port and diaphragm structure. Accordingly, the container and port system of this invention is economical to manufacture, thus presenting a substantial cost savings.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

What is claimed is:

1. A flexible, collapsible container for medical fluids composed of a flexible, inert, plastic material, said container comprising:

a body section of generally tubular configuration, said body section defining front, back, side and opposing end wall portions;

said end wall portions defining a hanger section at one end and a tubular portion with a diaphragm extending from the opposing end, said tubular portion being formed with a stepped parting line and said diaphragm being formed without a stepped parting line and having its thinnest dimension at the center thereof;

said body section being blow molded from a plastic resinous material with said tubular portion and said diaphragm being formed in a one-piece construction with said container, said diaphragm being positioned adjacent the outward end of said tubular portion, said tubular portion and said diaphragm being constructed and arranged to receive a piercing pin with portions of said pierced diaphragm in a fluid-tight manner;

whereby a fluid-tight connection can be effected between a flexible, collapsible container for medical fluids and an I.V. administration set.

2. The flexible, collapsible container as defined in claim 1 wherein said tubular portion includes a frusto-conical portion which flares outwardly toward the end of the tubular portion remote from said body section at the outer end thereof with said diaphragm positioned therein.

3. The flexible, collapsible container as defined in claim 2 wherein said diaphragm is formed in a concave manner with the smallest portion extending inwardly into said tubular portion.

4. The flexible collapsible container as defined in claim 2 wherein said diaphragm is positioned on the outward end of said frusto-conical portion and which further includes a straight wall portion extending from a diverging portion.

5. The flexible, collapsible container as defined in claim 2 further including a rubber reseal device secured to said frusto-conical portion.

6. A flexible collapsible container for medical fluids composed of a flexible, inert, plastic material, said container comprising:

a body section of generally tubular configuration when empty, having a longitudinal axis and a transverse axis shorter than said longitudinal axis;

said body section when filled with said medical fluid having a generally transverse oval configuration;

said body section further defining front, back, side and opposing end wall portions which are substantially smooth and unencumbered within the confines of said body section;

said end wall portions defining a hanger section at one end and a tubular portion with a diaphragm extending from the opposing end, said tubular portion being formed with a stepped parting line and said diaphragm being formed without a stepped parting line and having its thinnest dimension at the center thereof;

the side wall portions at said one end of said body section tapering from the outermost dimension of said body section to said hanger section to define shoulder portions;

said body section being blow molded from a plastic resinous material with said tubular portion and said diaphragm being formed in a one-piece construction with said container, said diaphragm being positioned adjacent the outward end of said tubular portion;

said tubular portion and said diaphragm constructed and arranged to receive a piercing pin with portions of said pierced diaphragm in a fluid-tight manner;

whereby a fluid-tight connection can be effected between a flexible, collapsible container for medical fluids with an I.V. administration set without the need for additional elements.

7. The flexible collapsible container as defined in claim 6 wherein said tubular portion includes a frusto-conical portion which flares outwardly toward the end of said tubular portion remote from said body section positioned at the outer end of said tubular portion with said diaphragm positioned within said tubular portion.

8. The flexible collapsible container as defined in claim 7 wherein said diaphragm is positioned outwardly of said frusto-conical portion and includes a straight wall portion extending from a diverging portion.

9. The flexible collapsible container as defined in claim 6 wherein said diaphragm is formed in a concave manner with the smallest diaphragm portion extending inwardly into said tubular portion.

10. The flexible collapsible container as defined in claim 6 further including a rubber reseal device secured to said frusto-conical portion.

* * * * *